United States Patent [19]

Neumeyer

[11] Patent Number: 4,543,256
[45] Date of Patent: Sep. 24, 1985

[54] (−)-10,1L METHYLENEDIOXY-N-N-PROPYLNORAPORPHINE AND METHODS EMPLOYING IT FOR INHIBITING THE EFFECTS OF EPILEPTIC SEIZURES AND FOR PREVENTION AND TREATMENT OF DUODENAL ULCERS

[75] Inventor: John L. Neumeyer, Wayland, Mass.

[73] Assignee: Northeastern University, Boston, Mass.

[21] Appl. No.: 379,557

[22] Filed: May 18, 1982

Related U.S. Application Data

[63] Continuation-in-part of Ser. No. 358,918, Mar. 17, 1982, abandoned, and a continuation-in-part of Ser. No. 358,917, Mar. 17, 1982, abandoned, which is a continuation-in-part of Ser. No. 346,841, Feb. 8, 1982, abandoned, which is a continuation-in-part of Ser. No. 274,772, Jun. 18, 1981, abandoned, which is a continuation-in-part of Ser. No. 148,179, May 8, 1980, abandoned.

[51] Int. Cl.[4] .................. A61K 31/485; C07D 221/18; C07D 491/06
[52] U.S. Cl. .................................. 514/280; 514/926; 546/48; 546/75
[58] Field of Search ................... 546/75, 48; 424/258, 424/260

[56] References Cited

U.S. PATENT DOCUMENTS

| | | | |
|---|---|---|---|
| 3,717,639 | 2/1973 | Neumeyer | 546/75 |
| 3,717,643 | 2/1973 | Archer | 546/75 |
| 3,810,987 | 5/1974 | Saari | 424/258 |
| 4,126,616 | 11/1978 | Hinshaw et al. | 546/75 |
| 4,425,350 | 1/1984 | Hartenstein et al. | 424/258 |

OTHER PUBLICATIONS

Anlezark et al., Psychopharmacology, 81, 135–139 (1983).
Baldessarini et al., European J. Pharmacol. 77, pp. 87–88 (1982).
Baldessarini, "Catecholamines: Basic and Clinical Frontiers", vol. 2, Proceedings of the Fourth International Catecholamine Symposium, Pacific Grove, Ca., 09/17-22/1978, Pergamon Press, pp. 1596–1598.
Bradbury et al., J. Pharm. Pharmacol. 35, pp. 494–499 (1983).
Campbell et al., Neuropharmacology, 21, pp. 953–961 (1982).
Campbell et al. (II), European J. Pharmacol., 67, pp. 139–142 (1980).
Granchelli et al. (II), J. Org. Chem., 42 (11), pp. 2014–2016 (1977).
Sperk et al., Neuropharmacology, vol. 21, pp. 1311–1316 (1982).
Szabo, The Lancet, Oct. 27, 1979, pp. 880–882 (1979).
Greene, "Protective Groups in Organic Synthesis", John Wiley & Sons, New York, pp. 108–110.

Neumeyer et al. (II), J. Med. Chem., 23, pp. 594–595 (1980).
Neumeyer et al. (III), J. Med. Chem., 24 (7), pp. 898–899 (1981).
Neumeyer et al., (IV), "Advances in Dopamine Research", Proceedings of a Satellite Symposium to the 8th International Congress of Pharmacology, Okayama, Japan, 7-81, Pergamon Press, pp. 291–295.

(List continued on next page.)

Primary Examiner—Donald G. Daus
Assistant Examiner—Diana G. Rivers
Attorney, Agent, or Firm—Weingarten, Schurgin, Gagnebin & Hayes

[57] ABSTRACT

A method for providing orally effective aporphine compounds, and new compounds which are orally effective in the prevention and treatment of duodenal ulcers and in the treatment of neurological and psychiatric disorders having the following formula

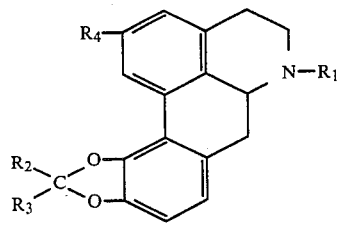

wherein $R_1$ is lower alkyl, substituted lower alkyl, cycloalkyl, substituted cycloalkyl, lower alkenyl, substituted lower alkenyl, lower alkynyl, substituted lower alkynyl, phenyl lower alkyl, phenyl lower alkenyl and phenyl lower alkynyl, $R_2$ and $R_3$ are hydrogen, methyl, lower alkyl, substituted lower alkyl, cycloalkyl, substituted cycloalkyl, lower alkenyl, substituted lower alkenyl, lower alkynyl, substituted lower alkynyl, phenyl lower alkyl, phenyl lower alkenyl and phenyl lower alkynyl and $R_4$ is hydrogen, hydroxy, —O—$R_5$ and

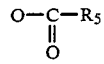

and $R_5$ is methyl and lower alkyl. Particularly effective are compounds wherein $R_4$ is hydrogen.

4 Claims, No Drawings

OTHER PUBLICATIONS

Smith et al., Research Communications in Chemical Pathology and Pharmacology, vol. 24, No. 3, Jun., 1979.

McOmie, Protective Groups in Organic Chemistry, Plenum Press, London and New York, (1973), pp. 121–122, 127–128, 150–151, 157–159.

Saari et al., J. Med. Chem., vol. 17, No. 10, pp. 1086–1090 (1974).

Neumeyer et al., J. Med. Chem., vol. 17, No. 10, pp. 1090–1095 (1974).

Granchelli et al., J. Org. Chem. vol. 46, pp. 2014–2017 (1977).

Ram et al., J. Org. Chem., vol. 46, pp. 2830–2831, Jun., 1981.

Lal et al., Chemical Abstracts, vol. 78, 92509j (1973).

Miller et al., Chemical Abstracts, vol. 84, 115631h (1976).

Iversen et al., Chemical Abstracts, vol. 87, 111272f (1977).

Fjalland et al., Chemical Abstracts, vol. 82, 38,708t (1975).

Sandor et al., Chemical Abstracts, vol. 87,227a (1977).

Uvnas-Wallenstein et al., Chemical Abstracts, vol. 89, 100153h (1978).

Bentley, Chemistry of the Morphine Alkaloids, Oxford, Clarendon Press 1954, p. 302.

(−)-10,1L METHYLENEDIOXY-N-N-PROPYLNORAPORPHINE AND METHODS EMPLOYING IT FOR INHIBITING THE EFFECTS OF EPILEPTIC SEIZURES AND FOR PREVENTION AND TREATMENT OF DUODENAL ULCERS

The invention described herein was made in the course of work under a grant or award from the Department of Health and Human Services.

BACKGROUND OF THE INVENTION

This present application is a continuation-in-part of my copending United States patent applications entitled respectively, Orally Effective Aporphine Compounds, Ser. No. 358,918, now abandoned, and Aporphine Compounds for Prevention and Treatment of Duodenal Ulcers Ser. No. 358,917, now abandoned, both filed Mar. 17, 1982, which in turn are continuations-in-part of my copending application 346,841, filed Feb. 8, 1982, now abandoned, which in turn is a continuation-in-part of my copending application, Ser. No. 274,772, filed June 18, 1981, now abandoned, which in turn is a continuation-in-part of my application, Ser. No. 148,179, filed May 8, 1980 and now abandoned, all said applications being incorporated herein by reference.

Many aporphine compounds have therapeutic activity. Thus, apomorphine (APO) and N-n-propylnoraporphine (NPA) have potent and selective actions at central and other dopamine receptor sites. Such aporphine compounds have been used clinically, especially in neurological and psychiatric disorders, but their clinical use has been limited by their poor oral bio-availability and short duration of action.

SUMMARY OF INVENTION

In accordance with this invention, an aporphine compound which has two adjacent hydroxy groups on an aromatic nucleus and which has a therapeutic effect when administered subcutaneously or intraperitoneally can be converted into an orally effective therapeutic compound by bridging the hydroxy groups to form a dioxy group as for example methylene dioxy. The dioxy group is cleaved in vivo to provide the compound with two adjacent hydroxy groups.

Therapeutic aporphine compounds having the following structure are particularly useful in this invention and are convertible to an orally effective therapeutic composition which is cleaved in vivo to release the compound with the two adjacent hydroxy groups

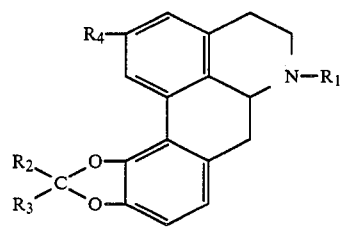

↓ in vivo

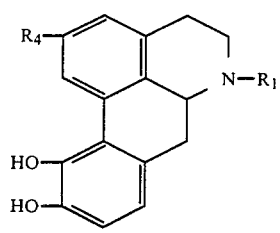

wherein $R_1$ is lower alkyl, substituted lower alkyl, cycloalkyl, lower alkenyl, substituted lower alkenyl, lower alkynyl, substituted lower alkynyl, phenyl lower alkyl, phenyl lower alkenyl and phenyl lower alkynyl, $R_4$ is hydrogen, hydroxy, —O—$R_5$ or

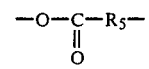

wherein $R_5$ is methyl, and lower alkyl and $R_2$ and $R_3$ are hydrogen, methyl and $R_1$.

This invention is also generally applicable to dopamine agonist compounds which have two hydroxy groups on adjacent positions on an aromatic nucleus and which have dopamine agonist activity when administered subcutaneously or interperitoneally. Such compounds include not only aporphine compounds but also non-aporphine compounds, as for example, compounds of the following structures:

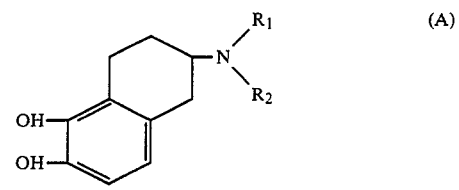

wherein $R_1$ and $R_2$ are hydrogen, methyl and lower alkyl

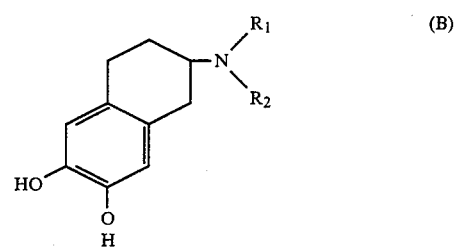

wherein $R_1$ and $R_2$ are hydrogen, methyl and lower alkyl

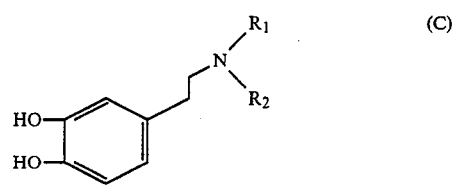

wherein $R_1$ and $R_2$ are hydrogen, methyl and lower alkyl.

Also, in accordance with the present invention aporphine compounds are described which are orally effective in treating neurological and psychiatric disorders. In addition aporphine compounds are described which are effective in the prevention and treatment of duodenal ulcers and can be administered orally, subcutaneously or peritoneally. Preferred examples of these novel compounds and dioxy groups have the following structures:

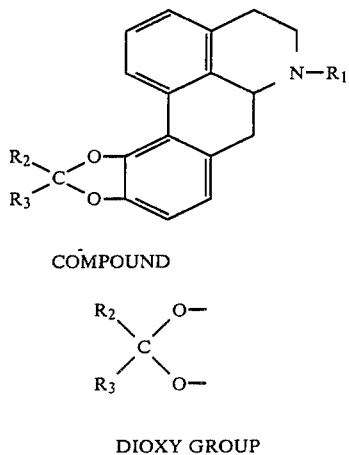

COMPOUND

DIOXY GROUP wherein $R_1$ is lower alkyl, substituted lower alkyl, cycloalkyl, substituted cycloalkyl, lower alkenyl, substituted lower alkenyl, lower alkynyl, substituted lower alkynyl, phenyl lower alkyl, phenyl lower alkenyl and phenyl lower alkynyl, and $R_2$ and $R_3$ are hydrogen, methyl, lower alkyl, substituted lower alkyl, cycloalkyl, substituted cycloalkyl, lower alkenyl, substituted lower alkenyl, lower alkynyl, substituted lower alkynyl, phenyl lower alkyl, phenyl lower alkenyl and phenyl lower alkynyl and pharmaceutically acceptable acid addition salts thereof.

In particular I have found that (—) 10, 11-methylenedioxy-N-n-propylnoraporphine is especially effective when administered orally in the prevention and treatment of duodenal ulcers and in the treatment of psychiatric and neurological disorders. I have also found that the methylene dioxy group is an especially effective dioxy group. It is believed that the compounds of this invention are converted in vivo to the dihydroxy compound and are orally effective and long acting.

As used herein, the term "lower-alkyl" means saturated monovalent aliphatic radicals, including straight and branched-chain radicals, of from two to six carbon atoms, as illustrated by, but not limited to ethyl, propyl, isopropyl, buty, sec.-butyl, amyl, or hexyl.

As used herein, the term "lower-alkenyl" means monovalent, aliphatic radicals of from three to seven carbon atoms which contain at least one double bond, and are either straight or branched-chain, as illustrated by, but not limited to 1-(2-propenyl), 1-(3-methyl-2-propenyl), 1-(1,3-dimethyl-2-propenyl), or 1-(2-hexenyl).

As used herein, the term "lower-alkynyl" means monovalent, alphatic radicals of from three to seven carbon atoms which contain at least one triple bond, and are either straight or branched, as illustrated by, but not limited to 1-(2-propynyl), 1-(1-methyl-2-propynyl), or 1-(2-heptynl).

As used herein, the term "cycloalkyl" means cyclic, saturated aliphatic radicals of from three to eight ring carbon atoms, as illustrated by, but not limited to cyclopropyl, cyclobutyl, 2-methylcyclobutyl, cyclohexyl, 4-methylcyclohexyl, or cyclooctyl.

As used herein, the terms "phenyl-lower-alkyl," "phenyl-lower-alkenyl," and "phenyl-lower-alkynyl" mean monovalent radicals consisting of a phenyl nucleus bonded to the rest of the molecule through, respectively, a divalent lower-alkylene radical of from one to four carbon atoms, as illustrated by, but not limited to methylene, 1,1-ethylene, 1,2-ethylene, 1,3-propylene, 1,2-propylene, or 1,4-butylene; or through a divalent lower-alkynylene radical of from two to four carbon atoms, as illustrated by, but not limited to 1,2-ethynylene, 1,3-propynylene, 1,3-(1-butynylene), and the like. Moreover the benzene ring of such phenyl-lower-alkyl, phenyl-lower-alkenyl, and phenyl-lower-alkynyl radicals can be substituted by one or more substituents selected from the group consisting of lower-alkyl, lower-alkoxy, halo(chloro, bromo, iodo, or fluoro), nitro, lower-alkylmercapto, methylenedioxy, and trifluoromethyl.

Apropriate acid addition salts are those derived from such diverse acids as formic acid, acetic acid, isobutyric acid, alpha-mercaptopropicnic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, benzenesulfinic acid, butylarsonic acid, p-toluenesulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

DOPAMINE AGONIST ACTIVITY

With respect to dopamine agonist activity, the compounds of this invention were tested for stereotyped gnawing behavior of rats in accordance with the techniques described in Baldessarini, R. J., (Walton, K. G. and Borgman, R. J. 1976), "Prolonged apomorphine-like behavioral effects of apomorphine ester." *Neuropharmacology* 15, 471.) In some rats forebrain tissue was assayed after administration of (—) 10,11-Methylenedioxy-N-n-Propylnoraphorphine (MDO-NPA) for the presence of free N-n-Propylnorapomorphine (NPA) by a sensitive and specific high-performance liquid chromatographic method with electrochemical detection (HPLC/ec). (Westerink, B. H. C. and Horn, A. S. 1979. "Do neuroleptics prevent the penetration of dopamine agonists into the brain?" *Eur. J. Pharmacol.* 58,39.) The results are shown in Table 1.

The compounds of this invention are very active in inducing stereotypy behavior in vivo when administered orally.

MDO-NPA at doses above 2 μmoles/kg, i.p. (about 0.68 mg/kg) produced dose-dependent increases in general motor activity NPA and APO exerted very similar effects on motor activity, with increased counts at doses above 2 μmoles/kg, but no significant effect at lower doses. In contrast, MDO-NPA induced inhibition of locomotor activity at doses below 2 μmoles/kg, with a maximum effect found at 0.3 μmole/kg (about 0.1 mg/kg). In addition, only MDO-NPA induced strong catalepsy at doses similar to those which inhibited general activity again, with a maximum effect found at 0.3 μmole/kg, i.p. (at the same molar dose, NPA and APO, respectively, produced only 15% and 7% as much stereotypy as MDO-NPA; N=12). Thus, MDO-NPA had a clearly biphasic pattern of activity in which low doses exerted significant motor-inhibiting and cataleptic effects resembling those of a classic neuroleptic, while higher doses exerted excitatory and stereotyped behaviors as expected of a typical DA agonist such as APO or NPA.

The duration of stereotyped behavioral effects of MDO-NPA exceeded that of NPA at doses above 1 μmole/kg, i.p., and MDO-NPA showed a consistent increase in duration of action with increased dose. The duration of behavioral action of NPA was about equal to, or slightly greater than that of APO, and both NPA and APO showed much less tendency for duration to increase with dose than did MDO-NPA When other derivatives of NPA or APO, with substituents at the methylene carbon or an electron-withdrawing group, such as a nitro function, in the 8-position were evaluated, MDO-APO showed relatively weak and inconsistent excitatory effects at a high dose (10 mg/kg, i.p.) and no significant behavioral effects after oral administration (1 to 5 mg/kg,).

Measurement of Biological Activity

Male Sprague-Dawley (Charles River Labs.) rats (initially 175–200 g) were housed four per cage, with free access to food and water, under controlled lighting (on 7:00 a.m. to 7:00 p.m.), constant temperature 21°–23° C. and controlled humidity (40–50%). Aporphines were administered, as described below, freshly dissolved in 1 mM citric acid mixed with 0.9% (w/v) saline (1:4, vols.); this solvent was also used as a vehicle ("placebo") control. Haloperidol was given in the same medium; 2-diethyl aminoethyl-2,2 diphenylvalerate HCl (SKF-525A) was given in saline.

Locomotor activity was evaluated by use of a printing electronic activity monitor (EAM, Stoelting Co., Chicago, IL) within a sound-attenuated chamber, typically for 60 min., as described previously (Stewart, Campbell, Sperk and Baldessarini, 1979, *Psychopharmacology* 60 281–289; Campbell and Baldessarini, 1981a, Psychopharmacology 73:219–222.

Stereotyped behavior was evaluated by a trained observer according to a rating scale method reported previously (Campbell and Baldessarini, 1981a). Briefly, the ratings were as follows: 0, no stereotypy, normal locomotion; 1, discontinuous sniffing, reduced locomotion; 2, continuous sniffing, only periodic exploration; 3, continuous sniffing, mouth movements, infrequent, exploratory activity, Ratings were made each 10 min. by observation for 30 sec, typically for 60 min. (maximum score=18.0/hour).

Catalepsy was assessed as described in detail elsewhere (Campbell and Baldessarini, 1981a; 1981b, *Life Sciences* 29 1341–46). Briefly, rats were evaluated every 10 min. by timing (stopwatch) their maintenance of an abnormal posture with forelimbs on a 1 cm-diameter steel bar parallel to, and 8 cm above the bench, so that the rat rested on its hindquarters only; 60 sec. was taken as a maximum and nearly all normal untreated rats remained on the bar for less than 5 sec. Ratings were made as follows: 0, remaining on the bar 0–10 sec; 1, 10–29 sec; 2, 30–59 sec; 3,>60 sec. Thus, in a typical 60 min. session, the maximum score was 18.0.

In all experiments except those which evaluated the time-course of drug effects, rats were given an injection of vehicle and then allowed to rest for 15 min. to adapt to nonspecific arousal effects, prior to a second injection of test agent (or placebo) and immediate behavioral testing. Behavioral data were evaluated by Student's t-test and are always expressed as mean ±SEM.

The following tables illustrate data evaluating the compounds of this invention for their dopamine agonist activity. Table 1 compares route of administration and stereotyped behavior among MDO-NPA and other aporphines. Table 2 denotes the effects of microsomal oxidase inhibitor on the behavioral effects of low and high doses of MDO-NPA. Table 3 evaluates the effects of haloperidol on stereotyped behavior induced by MDO-NPA. Table 4 compares characteristics of NPA and MDO-NPA. Table 5 compares MDO-NPA and analogs with respect to stereotyped behavior and locomotor activity.

TABLE 1

Route of administration and stereotyped response to MDO—NPA and other aporphines.

| Agent (1 mg/kg) | Stereotypy Score | | | Duration of Effect (min) | | |
|---|---|---|---|---|---|---|
| | P.O. | S.C. | I.P. | P.O. | S.C. | I.P. |
| MDO—NPA | 17.0 ± 1,2 | 17.5 ± 0.4 | 16.5 ± 0.8 | 112 ± 20 | 106 ± 10 | 116 ± 12 |
| NPA | 0 | 17.5 ± 0.8 | 17.5 ± 1.0 | 0 | 72 ± 6 | 70 ± 10 |
| APO | 0 | 17.5 ± 0.4 | 16.5 ± 2.4 | 0 | 70 ± 5 | 72 ± 12 |

Data are mean values ±SEM for N=6 rats per group given doses of each aporphine (1mg/kg/, or approximately 3 umole/kg) by orogastric intubation (P.O.), or subcutaneous (S.C.) or intraperitoneal (I.P.) injection. Stereotypy was rated for one hour as described in Methods and duration is defined as complete when scores diminished to ≦3 (out of a maximum possible score of 18).

TABLE 2

Effects of microsomal oxidase inhibitor (SKF-525A) on behavioral effects of low and high doses of MDO—NPA

| Dose of MDO—NPA (mg/kg) | Control | | SKF-525A | |
|---|---|---|---|---|
| | Activity | Stereotypy | Activity | Stereotypy |
| 0 | 409 ± 36 | 0 | 422 ± 28 | 0 |
| 0.05 | 190 ± 20 | ND | 425 ± 40* | ND |
| 0.10 | 130 ± 30 | ND | 415 ± 29* | ND |
| 0.20 | 260 ± 33 | ND | 410 ± 32* | ND |
| 0.30 | 435 ± 29 | 12.8 ± 0.6 | 440 ± 38 | 1.7 ± 0.6* |
| 1.0 | ND | 16.5 ± 0.1 | ND | 0.8 ± 0.2* |

TABLE 2-continued

Effects of microsomal oxidase inhibitor (SKF-525A) on behavioral effects of low and high doses of MDO—NPA

| Dose of MDO—NPA (mg/kg) | Control | | SKF-525A | |
|---|---|---|---|---|
| | Activity | Stereotypy | Activity | Stereotypy |
| 3.0 | ND | 16.2 ± 0.9 | ND | 0.8 ± 0.5* |

Data are mean values ±SEM (N=4 to 8 rats per condition). Animals were pretreated with SKF-525A (40 mg/kg, i.p.) or its vehicle 30 min before MDO-NPA (in the doses noted, from 0 to 3 mg/kg, i.p.). Activity was then monitored electronically for an hour after the low doses of MDO-NPA (data in counts/hour), or rated for stereotypy every 10 min for an hour after higher doses. N.D. indicates "not determined." (*) Indicates a significant difference by t-test between control and oxidase inhibitor-pretreated rats (p<0.01). In a control experiment, rats were pretreated with SKF-525A (40 mg/kg, i.p.) or its vehicle (N=6) as described and then given NPA (3 mg/kg, i.p.); the resulting stereotypy scores were 17.4±0.2 vs. 17.0±0.3 for controls vs. oxidase-inhibited rats, respectively, indicating no significant effect of the drug on actions of NPA itself.

TABLE 3

Effects of haloperidol on stereotyped behavior induced by MDO—NPA

| Haloperidol (mg/kg) | MDO—NPA (mg/kg) | |
|---|---|---|
| | 0.3 | 1.0 |
| 0 | 11.6 ± 0.8 | 16.6 ± 0.4 |
| 0.3 | 0.3 ± 0.2* | 0.5 ± 0.2* |
| 1.0 | 0.3 ± 0.2* | 1.2 ± 0.4* |

Haloperidol or its vehicle was given 30 min before MDO-NPA (both dissolved in the same citric acid-saline vehicle). Stereotypy was rated for 60 min as described in Methods. Data are means SEM (stereotypy scores, when 18=maximum in 1 hour) for N=6 rats per group; (*) indicates p<0.0001 by t test.

TABLE 4

Characteristics of NPA and MDO—NPA. Data are for stimulation of cAMP in rat striatal homogenates; inhibition of binding of [³H]APO to beef caudate synaptosomal membranes; stereotypy scores (maximum possible = 18.0; and cerebral levels of NPA by HPLC/ec; (*) p < 0.01.

| Condition | | $\bar{X}$ ± SEM (N) |
|---|---|---|
| Adenylate cyclase stimulation (cAMP, pmol/assay) | | |
| Control | (no addition) | 2.38 ± 0.14 (8) |
| NPA | (50 μM) | 5.67 ± 0.28 (4)* |
| MDO-NPA | (100 μM) | 2.92 ± 0.32 (4) |
| | (1000 μM) | 2.06 ± 0.30 (4) |
| IC₅₀ vs. [³H]APO binding (nM) | | |
| NPA | | 2.5 ± <0.2 (3) |
| MDO-NPA | | 850 ± <85 (3) |
| Stereotypy Score for 30 min after MDO—NPA (1 mg/kg) | | |
| i.p. | | 16.5 ± 1.2 (5) |
| p.o. | | 15.5 ± 1.6 (5) |
| Cerebral NPA (ng/g) at 30 min after MDO—NPA (1 mg/kg) | | |
| i.p. | | 6.0 ± 0.8 (3) |
| p.o | | 3.3 ± 1.8 (3) |

TABLE 5

Effects of analogs of MDO—NPA on stereotyped behavior and locomotor activity

| Compound | Substituents | | | Stereotypy | Locomotion |
|---|---|---|---|---|---|
| | R₁ | R₂ | R₃ | | |
| 8-Nitro-MDO—NPA | CH₃(CH₂)₂ | H | H | 4.4 ± 2.5 | 74.4 ± 9.8 |
| Methyl-ethyl MDO—NPA | CH₃(CH₂)₂ | CH₃ | CH₃CH₂ | 31.5 ± 1.9* | ND |
| Methyl-pentyl-MDO—NPA | CH₃(CH₂)₂ | CH₃ | CH₃(CH₂)₄ | 11.1 ± 5.7 | 86.1 ± 22.3 |

Data are mean values ±SEM (N=3 to 6 rats per condition) for effects of seven aporphine compounds (R=substituents, keyed to the structure above). Full chemical names for all compounds are provided in Methods. Ratings are expressed as percent of the maximum possible score (100%)=18.0) of stereotypy (Placebo-injected controls yielded scores of 4.4±2.5%); and as the percent of control locomotor activity (100%=430±86 counts/hr). Data are provided for a dose of 10 mg/kg (i.p.), although doses of 1 and 5 mg/kg were also tested.
(*) MDO-APO yielded a significant effect (p 0.01 by t-test) to inhibit locomotor activity at 10 mg/kg i.p., but induced weak and inconsistent stereotypy (not significant statistically); the methylethyl-substituted analog of MDO-NPA had weak stereotypic activity, the onset of which was delayed about 30 min and lasted about 60 min.
(ND=not determined).

ANTI-ULCEROGENIC ACTIVITY

Cysteamine- or propionitrile-induced duodenal ulcers in the rat have been shown to be suitable models to study the pathogenesis of acute and chronic duodenal ulcer disease as well as to test antiulcer drugs for therapeutic effect. Previous structure-activity, pharmacologic and biochemical studies in these laboratories have suggested the involvement of catecholamines, especially dopamine in the pathogenesis of experimental duodenal ulcer disease in the rat. A marked change in the incidence and intensity of cysteamine-induced duodenal ulcer was demonstrated by the administration of dopamine agonists or antagonists. Dopamine agonists (e.g., bromocriptine or lergotrile) administered either as a pre- or post-treatment, decreased the intensity of the acute and chronic duodenal ulcers and diminished the output of gastric acid in rats given cysteamine or propionitrile. The chemically induced duodenal ulceration was associated with changes in the sensitivity and number of dopamine receptors in the gastric and duodenal mucosa and muscularis propria. Pharmacologic limitations of available potent dopamine receptor agonists such as apomorphine and N-n-propylaporphine (NPA) are notably, short duration of action and poor oral bioavailability. We have found that (—) 10, 11-methylenedioxy-N-n-propylnoraporphine (MDO-NPA) is a unique, orally effective, and long acting apomorphine derivative that appears to act as a pro-drug of NPA to exert activity at dopamine receptors in the brain.

In rats given cysteamine, MDO-NPA caused significant prevention of experimental duodenal ulcers. The cysteamine-induced acute duodenal ulcers were virtually abolished by MDO-NPA in a dose and time-response manner: a single high dose of either MDO-NPA or NPA was active, while a daily treatment with small quantities virtually abolished the cysteamine-induced duodenal ulcers. The dopamine antagonist (+)-butaclamol aggravated the experimental duodenal ulcers and reversed the beneficial effect of NPA and MDO-NPA.

The groups consisted of 3-4 Sprague-Dawley female rats (160-180 ). Each experiment was repeated at least twice and the resulst of those groups were pooled. The dopamine agonists were injected s.c. once daily for seven days prior to the administration of cysteamine HCl (Aldrich) 28 mg/100 g p.o. three times with 3 hr. intervals. The animals were killed 48 hr after the duodenal ulcerogen. The intensity of duodenal ulcer was evaluated on a scale of 0-3, where 0=no ulcer, 1=superficial mucosal erosion, 2=transmural necrosis, deep ulcer, 3=perforated or penetrated duodenal ulcer. In the above table, MDO-NPA is converted in vivo to NPA, eg. N-n propylnorapomorphine.

TABLE 7

| | | EFFECT OF MDO—NPA ON CYSTEAMINE INDUCED GASTRIC ACID OUTPUT | | | | | | | | |
|---|---|---|---|---|---|---|---|---|---|---|
| GROUP | PRE-TREATMENT (A) | INITIAL OUTPUT (B) | 1 hr | 2 hr | 3 hr | 4 hr | 5 hr | 6 hr | 7 hr | TOTAL OUTPUT ($\mu$ Eq) |
| 1 | | 187 ± 20 | 68 ± 17 | 195 ± 48 | 141 ± 32 | 110 ± 25 | 104 ± 18 | 91 ± 12 | 99 ± 10 | 1043 ± 102 |
| 2 | MDO—NPA (0-1 mg/100 g. × 1 day) | 47 ± 13*** | 28 ± 18 | 66 ± 29 | 81 ± 40 | 17 ± 8* | 10 ± 3** | 20 ± 11** | 18 ± 6*** | 288 ± 67*** |
| 3 | MDO—NPA (0.1 mg/100 g. × 1 day, 1 week) | 120 ± 36 | 29 + 10 | 66 + 21* | 36 ± 9* | 14 ± 6** | 17 ± 7** | 18 ± 14** | 9 ± 4*** | 306 ± 62*** |

(A) In addition, rats of all groups were given cysteamine HCL, 15 mg. 100 g p.o. × 1, 30 min. after (the last dose of) MDO—NPA.
(B) At the opening of gastric fistula
\* = $P < 0.09$;
\*\* = $P < 0.01$;
\*\*\* = $P < 0.001$ The dopamine agonist MDO-NPA seems to exert prominent antiduodenal ulcerogenic effect. Its action is about 200 times more potent than the histamine $H_2$ receptor antagonist cimetidine. 10-fold more active than other dopamine agonists (e.g., bromocriptine, lergotrile), and its potency is identical to naturally occurring prostaglandins which also inhibit this experimental duodenal ulcer. Thus, MDO-NPA is a pro-drug with orally effective and prolonged activity at dopamine receptors (e.g., in duodenum and/or brain). The drug or one of its analogs may also have clinical utility for the prevention and/or treatment of duodenal ulcer disease.

As shown in Tables 6 and 7 MDO-NPA administered orally reduces the incidence and intensity of duodenal ulcers and the gastric acid output.

With respect to duodenal antiulcerogenic activity, the compound (−) 10, 11-methylenedioxy-N-n-propyl-noraporphine MDO-NPA was administered once daily for seven days to rats before the administration of cysteamine-hydrochloride which induces duodenal ulcers. Doses at the level of 50 or 100 micrograms per hundred grams of body weight were effective in preventing ulcers. This dosage is far less than any other known antiulcer compound which ordinarily required at least 0.2 milligrams per hundred grams of body weight.

TABLE 6

| | Effect of MDO—NPA or NPA on cysteamine-induced duodenal ulcer in the rat. | | | |
|---|---|---|---|---|
| | | Dose | Duodenal Ulcer | |
| Group | Pretreatment | ($\mu$g/ 100g) | Incidence (Positive/Total) | Intensity (Scale: 0–3) |
| 1. | Control | — | 10/12 | 1.8 |
| 2. | MDO—NPA | 50 | 4/6 | 0.8 |
| 3. | " | 100 | 3/6 | 0.5 |
| 4. | NPA | 50 | 2/9 | 1.1 |
| 5. | " | 100 | 6/9 | 0.9 |

SPECIFIC EXAMPLES OF INVENTION

EXAMPLE 1

Synthesis of (−) 10, 11-methylenedioxy-N-n-propylnoraporphine-HCl (MDO-NPA)

A solution of (−) N-n-propylnorapormorphine-hydrochloride (NPA) (2.0 g) in dimethylsulfoxide (DMSO) (16 ml, and aqueous NaOH (0.8 g in 8 ml of water) was treated with methylenebromide (1.2 g) under nitrogen. The resulting mixture was stirred for 4 h at 80° C., cooled and poured into ice water. The precipitate thus obtained was filtered, dried and extracted from ethyl acetate. Evaporation of the dried extract gave the crude product which was purified by column chromatography using silica gel and a mixture of ethyl acetate and methylene chloride (1:10 vols) as eluant. The free base thus obtained was converted into the hydrochloride salt with ethereal HCl to yield 0.75 g of product (36%), mp 245°-250° C. (dec.): mass spectrum, M+307; $[\alpha]_{546}^{22} -49.55$ (c 0.44 g in MeOH). Elemental analysis revealed: C, 99.7%; H, 103.4%, N, 97.3% of expected values calculated for $C_{20}H_{21}HO_2 \cdot HCl$. This was the compound used in the evaluation of MDO-NPA.

EXAMPLE 2

Synthesis of (−) 10, 11-methylenedioxy-N-n-propylnorapomorphine (MDO-NPA) from codeine The steps of synthesis is illustrated by the following scheme showing compounds A,B,C, D. E and F:

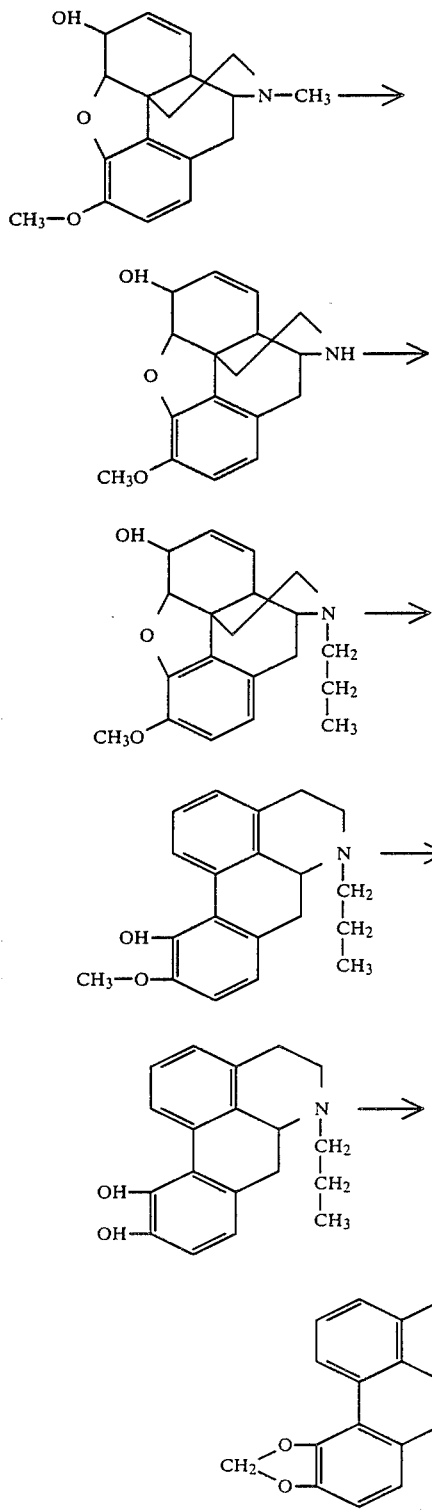

(A)

(B)

(C)

(D)

(E)

(F)

The first step, that of N-demethylation of codeine (A) to norcodeine (B) is well known in the art and can be carried out in various ways. The procedure described by G. A. Brine, K. G. Boldt, C. King Hart and F. I. Carroll in *Organic Preparations and Procedures Int.* 8 (3), 103–106 (1976) can be used conveniently. It uses methyl chloroformate to form the intermediate methyl carbamate of (A) and then hydrazine to cleave the carbamate to norcodeine (B).

Alkylation of norcodeine to produce the compound C can be carried out with n-propyl chloride, bromide, iodine, p-toluene-sulfonate etc. It can be carried in various appropriate solvents, some of them alcohols, such as methanol, ethanol, propanol, methoxyethanol, etc. Bases can be added as acid acceptor, such as pyridine, sodium or potassium carbonate or magnesium oxide. For the purpose of illustration, n-propyl iodide is used with ethanol as solvent in presence of anhydrous potassium carbonate. The N-n-propyl derivative (C) is obtained in quantitative yield.

Rearrangement of N-n-propyl-norapocodeine can be effected by treatment with various strong acids, such as the common mineral acids; e.g., sulfuric or hydrochloride acids, or with sulfonic acids, such as methanesulfonic acid or p-toluenesulfonic acid. Methanesulfonic acid used both as solvent and reagent affords a convenient mode of operating and can result in very high yields of the derived apocodeine. The intermediate of this invention, compound D can be obtained in yields of up to 98%.

Demethylation of the compound D can be realized with the use of such reagents as 48% aqueous hydrobromic acid, hydrobromic acid in acetic acid, boron trichloride or tribromide, etc. Best results are obtained using boron tribromide, both in higher yields (78%) and in quality of the material. Boron tribromide can be used in various solvents, but chloroform, chlorobenzene, or methylene chloride are preferred. The reaction requires only a short period of 15–60 minutes at 0° to 20° C.

The final step, that of formation of a methylene bridge between the two phenolic hydroxides can be accomplished with methylene chloride, bromide or iodide. Aprotic dipolar solvents can be employed, such as dimethylformamide, N-methylpyrrolidone or dimethylsulfoxide. In the example below a phase transfer method was employed, with methylene bromide in presence of alkali and with a quaternary ammonium salt as a catalyst. The method was first applied to catechols by A. P. Bashall and J. F. Collins in *Tetrahedron Letters*, No. 40, pp. 3489–3490 (1975). The reaction proceeds around 100° C. and is complete within two hours. An 80% yield of the desired compound F is obtained. As quaternary ammonium salt can be used tetra-n-butylammonium bromide, benzyltrimethylammonium bromide or a commercial mixed methyl trialkylammonium chloride, known under a trade name of Adogen 464.

In the following examples of preparation of Compounds C, D, E and F all temperatures are C (Celsius).

Compound C

A mixture of 19.3 g. (0.0678 mole) of norcordeine, 13.3 g. of n-propyl iodide (0.078 mole), 11.74 g. (0.085 mole) of anhydrous potassium carbomate and 150 ml. of 95% ethanol was stirred under reflux for 25 hours. Water (300 ml.) was added, the solution was extracted with four portions (150 ml; then 3×100 ml.) of chloroform and the extracts dried over anh. magnesium sulfate. Evaporation to dryness gave 22.15 g. (100% yield) of N-n-propylnorcodeine as a clear oil, which gave only one spot Rf~0.7 on TCL (silica with 10:1 CHCl$_3$/CH$_3$OH).

Compound D

N-n-propyl-norcodeine (22.15 g.; 0.0678 mole) was dissolved on warming in 120 ml. methanesulfonic acid and the mixture was stirred under nitrogen at 90°–95° (internal temperature) for one hour. The solution was cooled and diluted with 320 ml. of water, then neutralized with conc. ammonium hydroxide to pH 11 with stirring and cooling. A solid precipitated which was filtered, washed with water and dried in vacuo at 40° to constant weight. It sintered at 127° then melted at ca 185° TLC (silica with 20:1 $CH_3Cl_3/CH_3OH$) shows a green spot Rf 0.9. There was obtained 20.44 g (97.8% theory).

Whenever too rapid addition of ammonia caused the precipitate to oil, the oil was extracted with chloroform and the chloroform was shaken with successive portions of a sodium carbonate solution until all low Rf material seen on t.l.c. plate would disappear. The hydrochloride was formed quantitatively by addition of ethereal hydrogen chloride solution to a chloroform solution of the base. It sintered at 203° and melted at 215–22°.

Compound E

A solution of 2.0 g. (0.0058 mole) of N-n-propyl-norapocodeine hydrochloride in 15 ml methylene chloride was added dropwise under nitrogen, to 17.4 ml of a 1M solution of boron tribromide (0.00174 mole; three equivalents), stirred at +5°, over a period of 10 min. The cooling was removed and stirring continued at 20° for one hr. The solution was decanted from a small amount of precipitated tar, and 3.0 ml methanol was slowly added under stirring. After 15 min. excess anhydrous ether was added until precipitation was complete. The mixture was kept at 0° for one hr., the precipitate was filtered, and dried in vacuo to constant weight, yielding N-n-propylnorapomorphine hydrobromide (1.70 g.; 78.0% theory) as colorless solid, m.p. 270° after sintering at 260°. TLC on silica in 7:1 $CHCl_3/CH_3OH$ showed only one spot at Rf. 0.7.

Compound F

To a mixture of 6.9 g. (0.04 mole) of dibromomethane, 5 ml. water and 0.12 g. of Adogen 464 (0.00026 mole), vigorously stirred and heated under reflux under nitrogen, a solution of 10.0 g. (0.0265 mole) of N-n-propylnorapomorphine hydrobromide in 12.5 ml. water and 7.4 g. of a 50% solution of sodium hydroxide was added slowly over a period of two hours. After the addition was complete, the reaction mixture was stirred and refluxed for a further hour. After cooling methylene chloride (10 ml) was added, the solution was dried with magnesium sulfate and adsorbed on a silica gel column. Elution with methylene chloride gave the desired product. Ethereal hydrogen chloride was added to the main fraction of the eluant until the precipitation was complete. On drying in vacuo 8.23 g. (80.0% theory) of methylenedioxy-N-n-propylnorapomorphine hydrochloride was obtained as a colorless solid, m.p. 251°–253°.

EXAMPLE 3

Synthesis of (−) 8-nitro-10,11-methylenedioxy-N-n-propylnoraporphine -HCl (8-nitro-MDO-NPA)

MDO-NPA (80 mg) was added in small portions to 60% (vols) nitric acid (10 ml) with stirring. After 15 min., a clear solution formed and was stirred overnight. The reaction mixture was neutralized with aqueous NaOH (4%, w/v) and extracted from ether. The ethereal extract was washed with water, dried over $CaSO_4$, filtered and evaporated to dryness. The free base was converted into its hydrochloride salt by adding ethereal HCl to yield 50 mg. of product (55%), m.p. 225–229 C; $M^+$ 352, 351 (M+ −1); 323 $M^+ - C_2H_5$); 277 (323-$NO_2$). Elemental analysis yielded: C, 100.3%, H, 102.8%, N, 100.1% of values expected for $C_{20}H_{20}N_2O_4 \cdot HCl$.

EXAMPLE 4

(−) 10,11-Heptylidene-2-dioxy-N-n-propylnoraporphine-HCl (methyl-pentyl-MDO-NPA

A mixture of NPA (1.0 g) and heptanone-2 (1.0 g) was treated with $P_2O_5$ (1.0 g) at 25 C and then heated to 110 C for 2 h. The contents were cooled and left overnight at room temperature. The solid material was added to $Na_2CO_3$ solution (10%, w/v), stirred, and extracted in ether. The ethereal extract was dried over $CaSO_4$, filtered and evaporated to dryness. The crude material was chromatographed using silica gel and a mixture of ether: hexane (1:2, vols) as eluant to yield 300 mg. of base product (26%). The free base was converted to the hydrochloride salt by adding ethereal HCl to an ethereal solution of the base, m.p. 120–125 C. Elemental analysis yielded: C, 100.1% H, 103.9%; N, 98.5% of values expected for $C_{26}H_{32}NO_2 \cdot HCl$.

EXAMPLE 5

(−) 10, 11-Butylidene-2-dioxy-N-n-propylnoraporphine. HCl methyl-ethyl-MDO-NPA)

This compound was similarly prepared from NPA (1.0 g) and methylethyl ketone (0.8 g) to yield 200 mg (17%) of product, m.p. 150°–156° C. Elemental analysis yielded: C, 100.4%; H, 101.2%; N, 95.0% of expected values calculated for $C_{20}H_{20}N_2O_3 \cdot HCl$.

I claim:

1. (−) 10, 11-Methylenedioxy-N-n-propylnoraporphine and pharmaceutically acceptable acid addition salts thereof.

2. A method for inhibiting the effects of an epileptic seizure by administering orally a therapeutically effective amount of a compound of the formula shown in claim 1.

3. A method for prevention and treatment of a duodenal ulcer comprising administering a therapeutically effective amount of the compound of claim 1.

4. A method in accordance with claim 3 wherein the compound is administered orally.

* * * * *

UNITED STATES PATENT AND TRADEMARK OFFICE
CERTIFICATE OF CORRECTION

PATENT NO. : 4,543,256
DATED : September 24, 1985 (Page 1 of 4)
INVENTOR(S) : John L. Neumeyer It is certified that error appears in the above-identified patent and that said Letters Patent is hereby corrected as shown below:

<u>In the Title:</u> "(-)-10,1L METHYLENEDIOXY-N-N-" should read

--(-)-10,11 METHYLENEDIOXY-N-n- --

| | | |
|---|---|---|
| Column 2, line 29, | "interperitoneally" should read --intraperitoneally-- | |
| Column 3, line 7, | "peritoneally" should read --intraperitoneally-- | |
| Column 4, line 24, | "Apropriate" should read --Appropriate-- | |
| line 56, | "dioxy-N-n-Propylnoraphorphine" should read --dioxy-N-n-Propylnoraporphine-- | |
| Column 5, line 1, | "activity NPA" should read --activity. NPA-- | |
| line 33, | "(1 to 5 mg/kg,)." should read --(1 to 5 mg/kg).-- | |
| Column 6, line 3, | "activity," should read --activity.-- | |
| line 52, | "3 umole/kg)" should read --3 μmole/kg)-- | |
| Column 7, line 50, | "t test." should read --t-test.-- | |
| line 55, | "=18.0; and" should read -- =18.0); and-- | |
| line 56, | "(*) p" should read --(*) p < 0.01.-- | |
| Column 8, line 27, | "(100%) = 18.0)" should read --(100% = 18.0)-- | |
| line 68, | "crally" should read --orally-- | |

UNITED STATES PATENT AND TRADEMARK OFFICE
CERTIFICATE OF CORRECTION

PATENT NO. : 4,543,256 (Page 2 of 4)

DATED : September 24, 1985

INVENTOR(S) : John L. Neumeyer

It is certified that error appears in the above-identified patent and that said Letters Patent is hereby corrected as shown below:

Column 10, line 2, "(160-180)." should read --(160-180g).-- line 3, "resulst" should read --results-- lines 39-40, "Synthesis of (-) 10, 11-methylenedioxy-N-n-propylnoraporphine-HCl" should read --Synthesis of (-) 10, 11-methylenedioxy-N-n-propylnoraporphine-HCl-- line 43, "N-n-propylnorapormorphine" should read --N-n-propylnorapomorphine-- line 45, "(16 ml, and" should read --(16 ml), and-- lines 47-48, "4       should read    --4
 h at"                          hr at-- line 59, "$C_{20}H_{21}HO_2 \cdot HCl.$" should read --$C_{20}H_{21}NO_2 \cdot HCl.$-- lines 64-65, "Synthesis of (-) 10, 11-methylenedioxy-N-n" should read --Synthesis of (-) 10, 11-methylenedioxy-N-n-propylnorapomorphine-- line 67, "The steps of synthesis is" should read --The steps of synthesis are-- line 68, "A,B,C,D. E and F:" should read --A,B,C,D,E and F:--

Column 12, line 54, "norcordeine," should read --norcodeine,-- line 56, "carbomate" should read --carbonate--

UNITED STATES PATENT AND TRADEMARK OFFICE
CERTIFICATE OF CORRECTION

PATENT NO. : 4,543,256 (Page 3 of 4)
DATED : September 24, 1985
INVENTOR(S) : John L. Neumeyer It is certified that error appears in the above-identified patent and that said Letters Patent is hereby corrected as shown below:

Column 13, line 9, "185° TLC" should read --185°. TLC--
line 16, "t.l.c.," should read --TLC--

Column 14, line 4, "8-nitro-10," should read --8-Nitro-10,--
line 5, "(8-nitro-MDO-NPA)" should read --(8-Nitro-MDO-NPA)--
line 15, "323 $M^+-C_2H_5$);" should read --323 $(M^+ \div C_2H_5)$;--
lines 21-22, "(-) 10,11-Heptylidene-2-dioxy-N-n-propyl-noraporphine-" should read --(-) 10,11-Heptylidene-2-dioxy-N-n-propylnoraporphine.--
line 23, "HCl (methyl-pentyl-MDO-NPA" should read --HCl (methyl-pentyl-MDO-NPA)--

UNITED STATES PATENT AND TRADEMARK OFFICE
CERTIFICATE OF CORRECTION

PATENT NO. : 4,543,256 (Page 4 of 4)
DATED : September 24, 1985
INVENTOR(S) : John L. Neumeyer It is certified that error appears in the above-identified patent and that said Letters Patent is hereby corrected as shown below:

Column 14, lines 41-42   "(-) 10, 11-Butylidene-2-dioxy-N-n-propylnoraporphine. HCl" should read --(-) 10,11-Butylidene-2-dioxy-N-n-propylnoraporphine. HCl-- line 43,   "methyl-ethyl-MDO-NPA)" should read --(Methyl-ethyl-MDO-NPA)--

Signed and Sealed this

Twenty-fourth Day of June 1986

[SEAL]

Attest:

DONALD J. QUIGG

Attesting Officer

Commissioner of Patents and Trademarks